(12) United States Patent
Al-Harbi et al.

(10) Patent No.: US 10,338,014 B2
(45) Date of Patent: Jul. 2, 2019

(54) ESTIMATING FORMATION PROPERTIES USING SATURATION PROFILES

(71) Applicant: Saudi Arabian Oil Company, Dhahran (SA)

(72) Inventors: Ahmad Mubarak Al-Harbi, Dammam (SA); Hyung Tae Kwak, Dhahran (SA); Jun Gao, Al Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 140 days.

(21) Appl. No.: 15/661,852

(22) Filed: Jul. 27, 2017

(65) Prior Publication Data

US 2019/0033238 A1     Jan. 31, 2019

(51) Int. Cl.
   *G01N 24/08*        (2006.01)
   *G01R 33/44*        (2006.01)
   *G01N 1/34*          (2006.01)
   *G01R 33/46*        (2006.01)

(52) U.S. Cl.
   CPC ............. *G01N 24/081* (2013.01); *G01N 1/34* (2013.01); *G01R 33/448* (2013.01); *G01R 33/46* (2013.01)

(58) Field of Classification Search
   CPC ..... G01R 33/448; G01R 33/46; G01N 24/081
   See application file for complete search history.

(56) References Cited

U.S. PATENT DOCUMENTS

| | | | |
|---|---|---|---|
| 4,431,968 A | 2/1984 | Edelstein et al. | |
| 4,728,892 A | 3/1988 | Vinegar et al. | |
| 4,868,500 A | 9/1989 | Baldwin et al. | |
| 5,278,501 A | 1/1994 | Guilfoyle | |
| 6,415,649 B1 | 7/2002 | Spinier et al. | |
| 7,352,179 B2* | 4/2008 | Chen ...................... | G01N 24/08 324/303 |
| 9,018,950 B2 | 4/2015 | Li et al. | |

(Continued)

FOREIGN PATENT DOCUMENTS

GB       2505232 A       2/2014

OTHER PUBLICATIONS

Determination of nuclear magnetic resonance T2 cutoff value based on multifractal theory—An application in sandstone with complex pore structure. Xinmin Ge, Yiren Fan, Xuejuan Zhu, Yiguo Chen and Runze Li, Geophysics vol. 80, No. 1 Jan.-Feb. 2015, p. D11-D21 (Year: 2015).*

(Continued)

*Primary Examiner* — G. M. A Hyder
(74) *Attorney, Agent, or Firm* — Fish & Richardson P.C.

(57) ABSTRACT

Methods estimating a property of a porous media include: saturating a sample of the porous media; spinning the sample in a centrifuge with a first end of the sample closer to an axis of rotation of the centrifuge than a second end of the sample; obtaining a first estimate of the first property; saturating the sample of the porous media; spinning the sample in a centrifuge with the second end of the sample closer to the axis of rotation of the centrifuge than the first end of the sample; obtaining a second estimate of the first property; and determining the second property of the porous media based at least in part on the first estimate of the first property and the second estimate of the first property. The first property can be a $T_2$ distribution and the second property can be a $T_2$ cutoff.

23 Claims, 14 Drawing Sheets

(56) References Cited

U.S. PATENT DOCUMENTS

| | | | | |
|---|---|---|---|---|
| 9,389,193 | B1* | 7/2016 | Petrov | G01N 24/08 |
| 2013/0265043 | A1* | 10/2013 | Nicot | G01N 24/081 |
| | | | | 324/303 |
| 2014/0055134 | A1* | 2/2014 | Fordham | G01R 33/4818 |
| | | | | 324/309 |
| 2014/0285196 | A1* | 9/2014 | Liu | G01N 24/081 |
| | | | | 324/309 |
| 2015/0219782 | A1* | 8/2015 | Kadayam Viswanathan | |
| | | | | G01V 3/32 |
| | | | | 324/309 |
| 2016/0341680 | A1* | 11/2016 | Kadayam Viswanathan | |
| | | | | G01N 24/081 |
| 2019/0033239 | A1* | 1/2019 | Gao | G01R 33/448 |

OTHER PUBLICATIONS

"NMR log calibration from laboratory core measurements," Application Note 3, Oxford Industrial Analysis, 2015, 4 pages.

"Porosity determination with NMR logging," available on or before Jun. 24, 2015, retrieved from URl <https://petrowiki.org/Porosity_determination_with_NMR_logging>, 6 pages.

"Routine Core Analysis—Free fluid, bound fluid and T2cutoff," Application Note 3, Magritek, available on or before Apr. 17, 2017, 5 pages.

Haldia et al., "A new approach to determine T2 cutoff value with integration of NMR, MDT pressure data in TS-V sand of Charali field," P013, 10th Biennial International Conference and Exposition, Kochi 2013, 8 pages.

Hassler and Brunner, "Measurement of Capillary Pressures in Small Core Samples," Petroleum Technology, Los Angeles Meeting, Oct. 1944, 10 pages.

Ge et al., "Determination of nuclear magnetic resonance T2 cutoff value based on multifractal theory—An application in sandstone with complex pore structure," Geophysics, Society of Exploration of Geophysics, vol. 80, No. 1, Apr. 1, 2015, 11 pages.

Anonymous, "NMR and Core Analysis," retrieved from URL: <http://www.greenimaging.com/wp-content/uploads/3374_MR_GeoSpec_Technical_Datasheet_Web.pdf>, retrieved on Oct. 23, 2018, available on or before 2015, 8 pages.

International Search Report and Written Opinion issued in International Application No. PCT/US2018/043287 dated Nov. 6, 2018, 15 pages.

Hassler et al., "Measurement of Capillary Pressures in Small Core Samples," Oct. 1944, 10 pages.

Petrov et al., "T2 Distribution Mapping Profiles with Phase-Encode MRI," Journal of Magnetic Resonance, Published in 2011, 9 pages.

Vashaee et al., "Local T2 Measurement Employing Longitudinal Hadamard Encoding and Adiabatic Inversion Pulses in Porous Media," Journal of Magnetic Resonance, Published in 2015, 8 pages.

Spinler et al., "Capillary Pressure Scanning Curves by Direct Measurement of Saturation," Published in 1997, 13 pages.

Vashaee, "A Comparison of Magnetic Resonance Methods for Spatially Resolved T2 Distribution Measurements in Porous Media," Apr. 2015, 18 pages.

Li, "Spin Echo SPI Methods for Quantative Analysis of Fluids in Porous Media," Published in 2009, 10 pages.

Petrov et al., "Local T2 Distribution Measurements with DANTE-Z Slice Selection," Abstract, Feb. 2012, 3 pages.

Enwere, "Some Insight into Laboratory Core Floods using an NMRI Technique," Abstract, Jun. 1994, 2 pages.

Costa Gomes et al., "Reservoir Rocky Typing Using NMR & Centrifuge," retrieved from URL <http://www.jgmaas.com/SCA/2014/SCA2014-096.pdf>, retrieved on Oct. 23, 2018, available on or before Sep. 8, 2014, 6 pages.

Kwak et al., "The Methods of Correcting NMR Data from Dry Glass Wells Drilled with Format Based Muds by Advanced NMR Techniques," Society of Petroleum Engineers—SPE Kingdom of Saudi Arabia Annual Technical Symposium and Exhibition, Apr. 24, 2017, 16 pages.

Nadia Testamanti et al., "Determination of NMR T2cut-off for clay bound water in shales: A case study for Carynginia Formation, Perth Basin, Western Australia," Journal of Petroleum Science and Engineering, vol. 149, Jan. 20, 2017, 7 pages.

International Search Report and Written Opinion issued in International Application No. PCT/US2018/043285 dated Nov. 7, 2018, 17 pages.

* cited by examiner

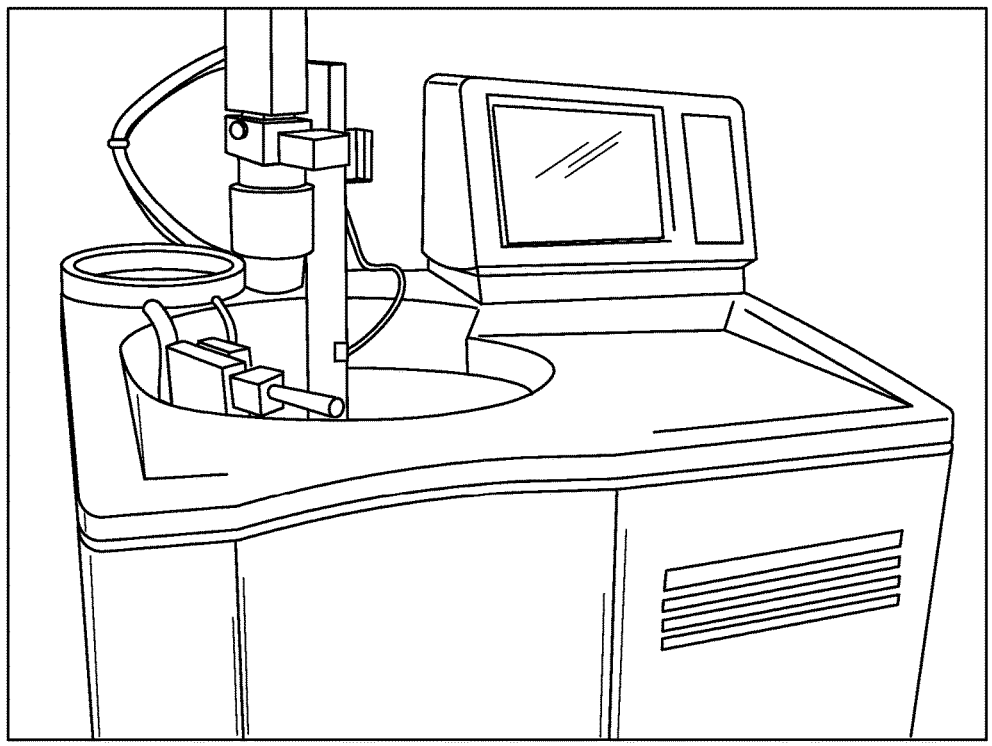
FIG. 4A
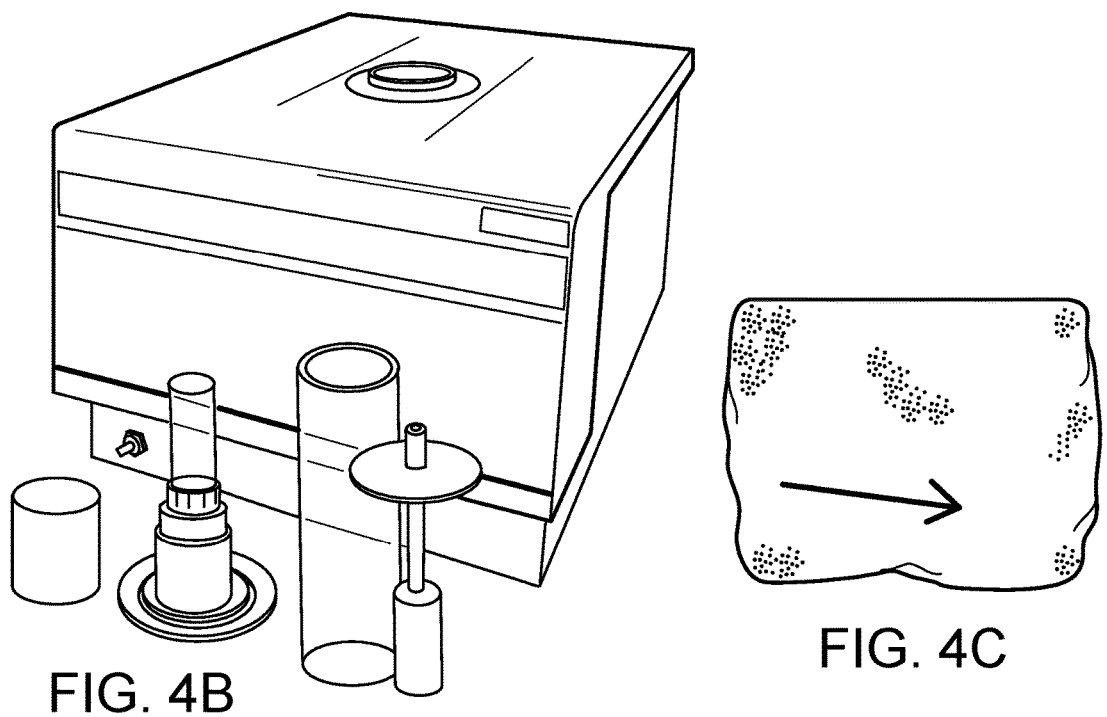
FIG. 4B
FIG. 4C

ESTIMATING FORMATION PROPERTIES USING SATURATION PROFILES

TECHNICAL FIELD

This invention relates to estimating formation properties, and more particularly to estimating formation properties using nuclear magnetic resonance (NMR) techniques.

BACKGROUND

NMR logging techniques are sometimes used in estimating formation porosity and associated characteristics. NMR logging measures the induced magnet moment of hydrogen nuclei contained within the fluid-filled pore space of the formation. NMR logs provide information about the quantities of fluids present, the properties of these fluids, and the sizes of the pores containing these fluids.

NMR logging has the advantage of measuring only the response of the presence of hydrogen protons contained in oil, water and gas without interference from the matrix minerals. NMR logs can provide the information about the fluids and the interaction between the fluids and rock. The $T_2$ spectrum, inverted from the time domain relaxation time profile, is a reflection of the pore size distribution which makes it possible to differentiate clay-bound water (CBW), bulk volume of the irreducible (BVI) water and free water index (FFI) for accurate estimation of recoverable reserves and to infer the permeability using Coates or Schlumberger models.

In NMR, $T_2$ is a time constant which characterizes transverse relaxation of an NMR signal. $T_2$ cutoff is a parameter used in interpretation of the NMR logging to distinguish the bulk volume of irreducible water (BVI) and free fluids (FFI). The BVI and FFI are used in calculation of recoverable reserve and, in the free fluid model, for estimating permeability.

SUMMARY

The methods and systems described in this disclosure improve measurement of properties of porous media such as, for example, $T_2$ cutoff determination by using saturation profiles, slice selection $T_2$, and spatial $T_2$. In the laboratory, the $T_2$ cutoff is determined by comparing a $T_2$ spectrum of a sample at 100% saturation with the same sample at irreducible saturation. Centrifuge spinning is commonly used to obtain the irreducible state due to its time efficiency. These methods and systems incorporate the saturation profile to identify the real irreducible water segment and use $T_2$ of the selected slice to measure only the irreducible segment. The identification of the irreducible water segment can reduce or eliminate the operational uncertainty of determining the spinning speed. In addition, this approach can provide variable $T_2$ cutoff for different displacement pressures.

These methods and systems can provide a more accurate determination of properties of interest than methods which are based on the assumption that average saturation across the whole sample represents irreducible water conditions. This assumption is frequently inaccurate for low permeability rocks because of the saturation gradient existing along the length of the core sample as a result of different centrifugal forces along the length of the sample after being desaturated at a certain centrifuge speed. This results in overestimation of BVI, which means underestimation of the recoverable reserve. In the case of high permeability samples, the saturation gradient is expected to be much less severe than that of low permeability rocks and usually can be ignored because it has less effect on the estimation of $T_2$ cutoff. In order to obtain a more accurate $T_2$ cutoff value from a low permeability rock, methods that don't use identification of the irreducible water segment can require the rock to be spun at high centrifuge speed more than needed. For low permeability limestone rocks (chalky-like), this can be an issue as these rocks are fragile and, by centrifuging at high speed, grains start to get loose leading to inaccurate data and perhaps destruction of the rock.

"Irreducible water saturation" is commonly used in reference to the saturation of a core sample at which water production slows or stops even with an increase in the spinning rate. When irreducible water saturation has been achieved, the actual saturation profile typically has a gradient. This disclosure uses "real irreducible water segment" and "low-saturation portion" to refer to a segment near the invading end of the sample in which conditions approach actual irreducible water saturation.

Numerous experiments show that for typical sandstones the $T_2$ cutoff is around 33 ms. The $T_2$ cutoff of typical carbonates varies from 80 to 120 ms with an average value of 92 ms. In many cases, the direct use of these values can generate satisfactory results without measuring them in the laboratory. However, for samples with complex lithology and pore systems $T_2$ cutoff need to be usually determined in the laboratory.

In one aspect, methods of estimating a $T_2$ cutoff of a porous media include: saturating a sample of the porous media with a fluid; measuring a $T_2$ distribution of the sample while saturated; preparing the sample for unsaturated measurement by: spinning the sample in a centrifuge with a first end of the sample closer to an axis of rotation of the centrifuge than a second end of the sample; obtaining a saturation profile of the sample; and identifying a first low-saturation portion of the sample; measuring a $T_2$ distribution of the porous media on the first low-saturation portion of the sample; obtaining a first estimate of the $T_2$ cutoff of the porous media by comparing the $T_2$ distribution measured on the first low-saturation portion of the sample with the $T_2$ distribution measured under saturated conditions; saturating the sample of the porous media with the fluid; measuring a $T_2$ distribution of the sample while saturated; preparing the sample for unsaturated measurement by: spinning the sample in a centrifuge with the second end of the sample closer to the axis of rotation of the centrifuge than the first end of the sample; obtaining a saturation profile of the sample; and identifying a second low-saturation portion of the sample; measuring a $T_2$ distribution of the porous media on the second low-saturation portion of the sample; obtaining a second estimate of the $T_2$ cutoff of the porous media by comparing the $T_2$ distribution measured on the second low-saturation portion of the sample with the $T_2$ distribution measured under saturated conditions; and averaging the first estimate of the $T_2$ cutoff and the second estimate of the $T_2$ cutoff. As used here, measuring a $T_2$ distribution include measuring a spatial $T_2$ distribution.

In one aspect, methods of estimating a $T_2$ cutoff of a porous media include: saturating a sample of the porous media with a fluid; measuring a $T_2$ distribution of the sample while saturated; preparing the sample for unsaturated measurement by: spinning the sample in a centrifuge with a first end of the sample closer to an axis of rotation of the centrifuge than a second end of the sample; obtaining a saturation profile of the sample; and identifying a first low-saturation portion of the sample; measuring a $T_2$ distribution of the porous media on the first low-saturation portion of the sample; and obtaining a first estimate of the $T_2$ cutoff of the porous media by comparing the $T_2$ distribution measured on the first low-saturation portion of the sample with the $T_2$ distribution measured under saturated conditions.

In one aspect, methods of estimating a property of a porous media include: saturating a sample of the porous media with a fluid; spinning the sample in a centrifuge with a first end of the sample closer to an axis of rotation of the centrifuge than a second end of the sample; measuring a first property of the porous media to obtain a first estimate of the first property; saturating the sample of the porous media with the fluid after obtaining the first estimate of the first property; spinning the sample in a centrifuge with the second end of the sample closer to the axis of rotation of the centrifuge than the first end of the sample; measuring the first property of the porous media to obtain a second estimate of the first property; and determining the second property of the porous media based at least in part on the first estimate of the first property and the second estimate of the first property.

Embodiments of these methods can include one or more of the following features.

In some embodiments, obtaining the saturation profile of the sample comprises performing NMR measurements on the sample.

In some embodiments, methods include determining that the sample is heterogeneous. In some cases, determining that the sample is heterogeneous comprises comparing a maximum porosity and a minimum porosity of the sample.

In some embodiments, identifying the first low-saturation portion of the sample comprises identifying a portion of the sample in which saturation of the sample is within 10% of a minimum saturation of the sample.

In some embodiments, methods include comparing the $T_2$ distribution measured on the first low-saturation portion of the sample with the $T_2$ distribution measured under saturated conditions comprises comparing the $T_2$ distribution measured on the first low-saturation portion of the sample with a portion of the $T_2$ distribution measured under saturated conditions that corresponds with the first low-saturation portion of the sample. In some cases, methods include: saturating the sample of the porous media with the fluid; measuring a $T_2$ distribution of the sample while saturated; preparing the sample for unsaturated measurement by: spinning the sample in a centrifuge with the second end of the sample closer to the axis of rotation of the centrifuge than the first end of the sample; obtaining a saturation profile of the sample; identifying a second low-saturation portion of the sample; measuring a $T_2$ distribution of the porous media on the second low-saturation portion of the sample; obtaining a second estimate of the $T_2$ cutoff of the porous media by comparing the $T_2$ distribution measured on the second low-saturation portion of the sample with the $T_2$ distribution measured under saturated conditions; and averaging the first estimate of the $T_2$ cutoff and the second estimate of the $T_2$ cutoff.

In some embodiments, methods include measuring the first property of the porous media after saturating the sample and before spinning the sample to obtain the first estimate of the first property. In some cases, the first property and the second property are different properties. In some cases, the first property is a $T_2$ distribution. IN some cases, the second property is a $T_2$ cutoff of the porous media.

In some embodiments, determining the second property of the porous media comprises calculating a first estimate of the second property based on the first estimate of the first property, calculating a second estimate of the second property based on the second estimate of the first property, and averaging the first estimate of the second property and the second estimate of the second property.

In some embodiments, measuring a first property of the porous media to obtain a first estimate of the first property comprises identifying a low-saturation portion of the sample and measuring a first $T_2$ distribution of the porous media on the identified portion of the sample. In some cases, measuring a first property of the porous media to obtain a second estimate of the first property comprises identifying a low-saturation portion of the sample and measuring a second $T_2$ distribution of the porous media on the identified portion of the sample. In some cases, methods include calculating a first estimate of a $T_2$ cutoff of the porous media based the first $T_2$ distribution, calculating a second estimate of the $T_2$ cutoff of the porous media based the first $T_2$ distribution of the porous media, and averaging the first estimate of the $T_2$ cutoff and the second estimate of the $T_2$ cutoff. Identifying the low-saturation portion of the sample can include performing NMR measurements on the sample.

These methods can improve the accuracy of formation properties such as, for example, $T_2$ cutoff, BVI, FFI and derived NMR permeability. Both from centrifugal theory and direct observation of the saturation profiles shows that the saturation at the producing end of a centrifuged sample is significantly higher than the saturation at the invading end (irreducible water saturation segment). Both the $T_2$ spectrum and average saturation from mass balance from the whole core contains segments with significantly larger saturation unless the permeability or the spinning speed are very high. In contrast to methods that measure the $T_2$ spectrum after centrifuge spinning on the whole core sample, the methods of this disclosure perform the $T_2$ measurement on the portion of the sample that is at the irreducible state. This approach can avoid the systematic overestimation of the $T_2$ cutoff and irreducible water saturation that occurs when values for the whole sample are used.

These methods also provide a data-based approach to selecting spinning speed of a centrifuge for dewatering a core sample rather than selecting spinning speed by trial and error. This can reduce or eliminate the operational uncertainty inherent in selecting the spinning speed either by trial and error or one speed based on permeability. In addition, this approach can avoid the extra steps needed to verify the non-uniform irreducible water state in the trial and error methods.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A, 4B, and 4C show components of a system operable to implement the method of FIG. 1.

Like reference symbols in the various drawings indicate like elements.

DETAILED DESCRIPTION

The methods and systems described in this disclosure provide an approach to determining properties (for example, $T_2$ cutoff) of a porous media based on measurements of at least one property of the porous media in a low-saturation portion of a sample of the porous media. Observations in the low-saturation portion of the sample provide a better foundation for calculations that assume irreducible water conditions than observations across the entire sample.

In the following example, a method of determining properties of a porous media based on measurements of at least one property of the porous media in a low-saturation portion of the sample is applied to estimation of the $T_2$ cutoff of a formation. However, the method can also be applied to the estimation of other parameters measured with the assumption of uniform saturation distribution such as, for example, resistivity and capillary pressure by porous plate.

Figure 1:
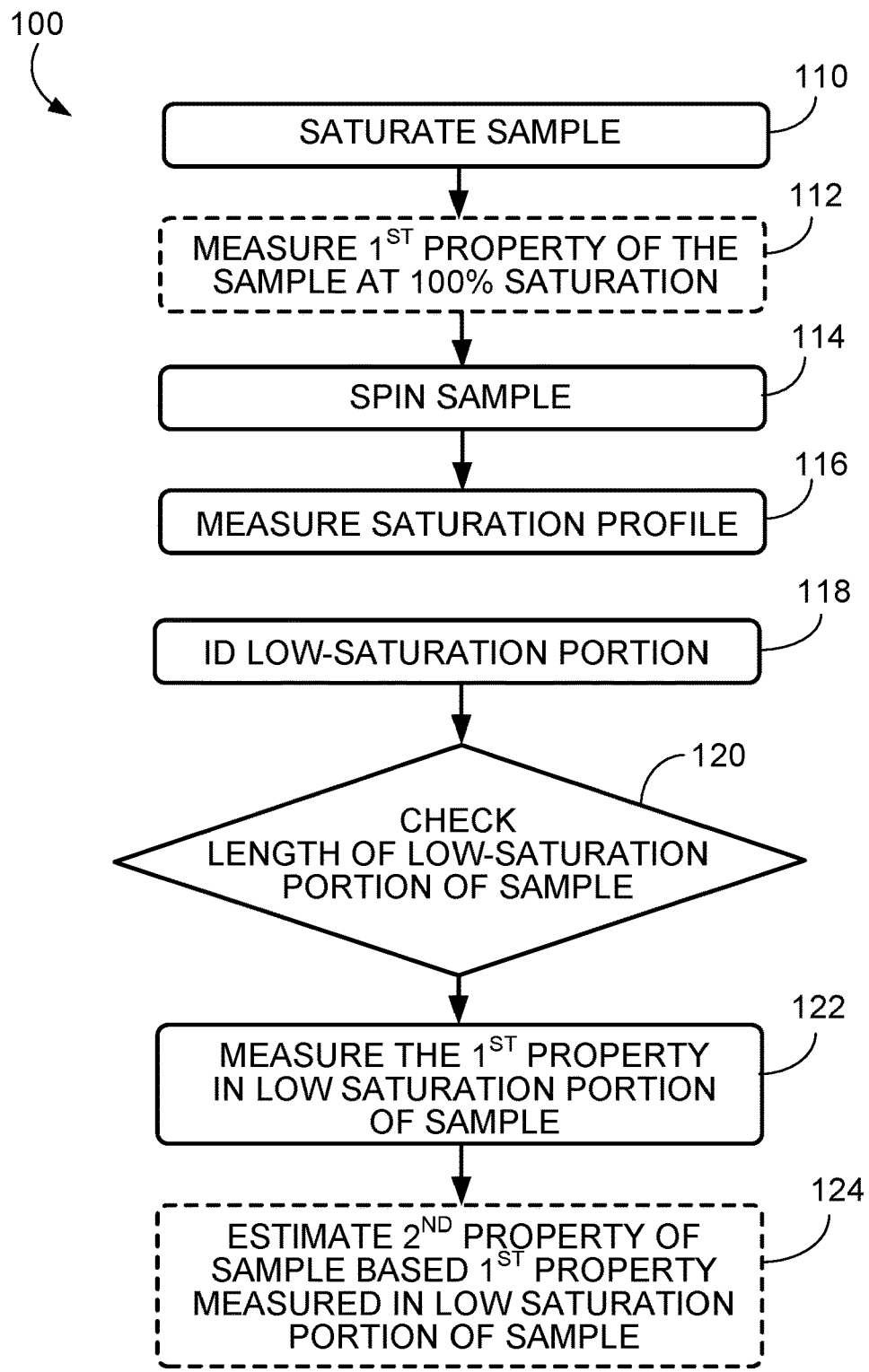
FIG. 1 illustrates a method of determining properties of a sample.

FIG. 1 illustrates a method 100 of estimating a property of a porous media. The method 100 includes saturating a sample of the porous media with a fluid 110. A first property of the porous media is measured on the saturated sample 112 if characteristics at saturation are used in subsequent calculations. The sample is spun in a centrifuge to remove fluid 114. The initial spinning speed can be selected based on the permeability of the sample. The J function, as known as the Leverett J-function, is a dimensionless function based on capillary pressure and other parameters and can be used to estimate the initial spinning speed. For example, a J function of 3 is typically appropriate. The Leverett J equation is:

$$J = \frac{P_C \sqrt{\frac{k}{\varnothing}}}{\sigma \cos\theta} \quad (1)$$

$$P_C = \frac{1}{2}\Delta\rho\omega^2(r_1^2 - r_2^2) \quad (2)$$

Where k is the permeability, $\varnothing$ is the porosity, $\sigma$ is the interfacial Tension (72 is used for air/water systems), $\theta$ is the contact angle (zero is assumed), $P_C$ is the capillary pressure, J is the Leverett J number, $\Delta\rho$ is density difference between air and water, $\omega$ is centrifuge speed, $r_1$ and $r_2$ are distance from centrifuge center of rotation to the bottom end of the core and distance from centrifuge center of rotation to the top of the core, respectively.

Thus, $P_C$ can be calculated for a certain J number using equation (1), and then $\omega$ is estimated from equation (2).

After spinning, a saturation profile of the sample is measured 116 and used to identify a low-saturation portion of the sample 118. The length of the low-saturation portion of the sample is checked 120 to verify that the length exceeds a minimum. If the length of the low-saturation portion of the sample does not exceed the minimum length, the sample is spun at a higher speed before measurement of the saturation profile with spinning, identification of the low-saturation portion of the sample, and checking the length repeated until the length of the low-saturation portion of the sample exceeds the minimum. When the length of the low-saturation portion of the sample exceeds the minimum, the first property of the porous media is measured in the identified portion of the sample 122. Optionally, a second property of the porous media is determined based at least in part on the first property measured in low saturation portion of sample 124.

In one application, method 100 can be applied to a core sample from a formation to estimate the $T_2$ cutoff of the formation. A cleaned and dried core sample from a formation of interest is saturated with brine. After saturation, NMR techniques are used to obtain a saturation profile and a $T_2$ spectrum/spatial $T_2$ of the saturated sample. The saturation profile and the slice selection $T_2$ distribution can be acquired by applying magnetic field gradient along with the polarization magnetic field as described by Vashaee, S., B. Newling, and B. J. Balcom in "Local $T_2$ measurement employing longitudinal Hadamard encoding and adiabatic inversion pulses in porous media." Journal of Magnetic Resonance 261 (2015): 141-148. Although most new NMR instruments have the magnetic gradient needed for measuring the saturation profile, some older NMR instruments do not have this capability.

The sample is spun in a centrifuge to remove fluid 114. After spinning, a saturation profile of the sample is measured 116 using NMR techniques and used to identify a low-saturation portion of the sample 118.

As discussed previously, the length of the low-saturation portion of the sample is checked to verify that the length of the low-saturation portion of the sample exceeds a minimum length. The minimum length is sample specific and can be, for example, a set distance or a percentage of the total sample length. Core samples are typically ~2 inches (~5 cm) long and ~1 inch (~2.5 cm) in diameter. For these size samples, a minimum length of the low-saturation portion of the sample of 0.4 inches (1 cm) has been found to be appropriate. When the length of the low-saturation portion of the sample exceeds 1 cm, the $T_2$ spectrum of the of the low-saturation portion of the sample is measured and then used as the basis for estimation of the $T_2$ cutoff using the procedure explained with reference to FIG. 2. Some approaches to implementing the method 100 set the minimum as a percentage of the sample length (for example, >30%, >40%, >50%, or >60%). The identification and length check can also be performed visually manually by an operator.

Figure 2:
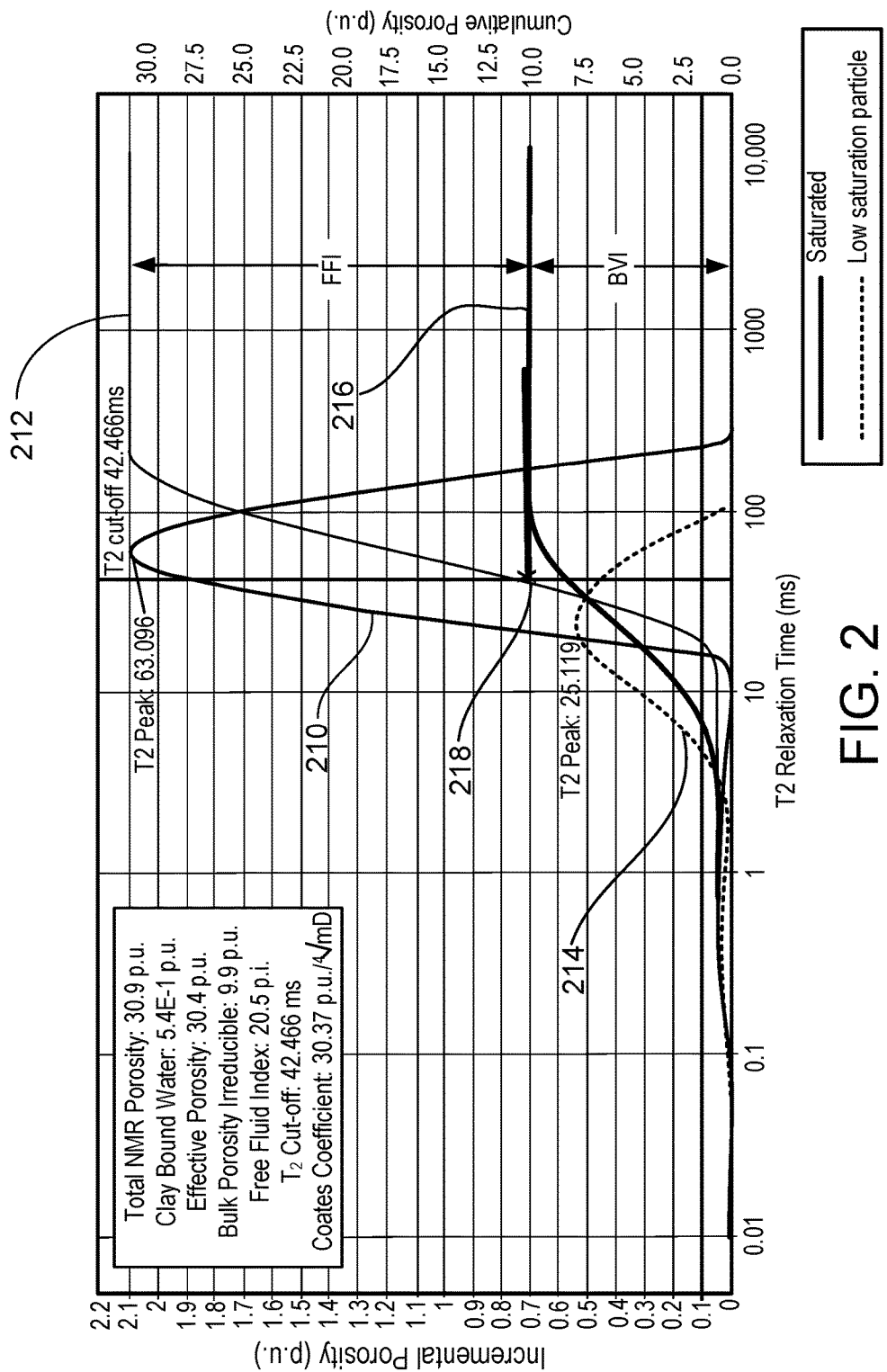
FIG. 2 includes spectra of fully saturated and desaturated core sample.

FIG. 2 shows a chart in which the incremental porosity of $T_2$ spectra (left vertical axis) and the cumulative porosity of cumulative curves (right vertical axis) are plotted as function of $T_2$ relaxation time. A $T_2$ spectrum 210 and a cumulative curve 212 obtained from a core sample under fully saturated conditions and a $T_2$ spectrum 214 and a cumulative curve 216 obtained from the low-saturation portion of the core sample (for example, as described with respect to FIG. 1) are displayed on this chart. The plateau of the low-saturation cumulative curve 216 is extended to the left to an intersection 218 with the saturated cumulative curve 212. The $T_2$ cutoff is taken to be the $T_2$ relaxation time of the intersection 218 at which the cumulative value on the saturated curve 212 equals the final cumulative value of the unsaturated curve 216. For this sample, the $T_2$ cutoff is 42.400 ms. The area covered by the $T_2$ spectrum at low-saturation equals to the partial area of 100% water saturation spectrum at the left of the vertical line which is the BVI and the partial area at the right of the vertical line is the FFI. The permeability can be derived from these parameters using models such as Timur-Coates.

For the high permeability samples, the entire sample may be at low-saturation conditions and the saturated and low-saturation curves can be compared directly. If only a portion of the sample is at low-saturation conditions, the $T_2$ spectrum for the low-saturation portion of the sample must be normalized. The $T_2$ spectrum of the low-saturation portion is converted to the whole core by a ratio of core length to the low-saturation portion length and the converted spectrum is compared with the spectrum at 100% saturation.

Figure 3:
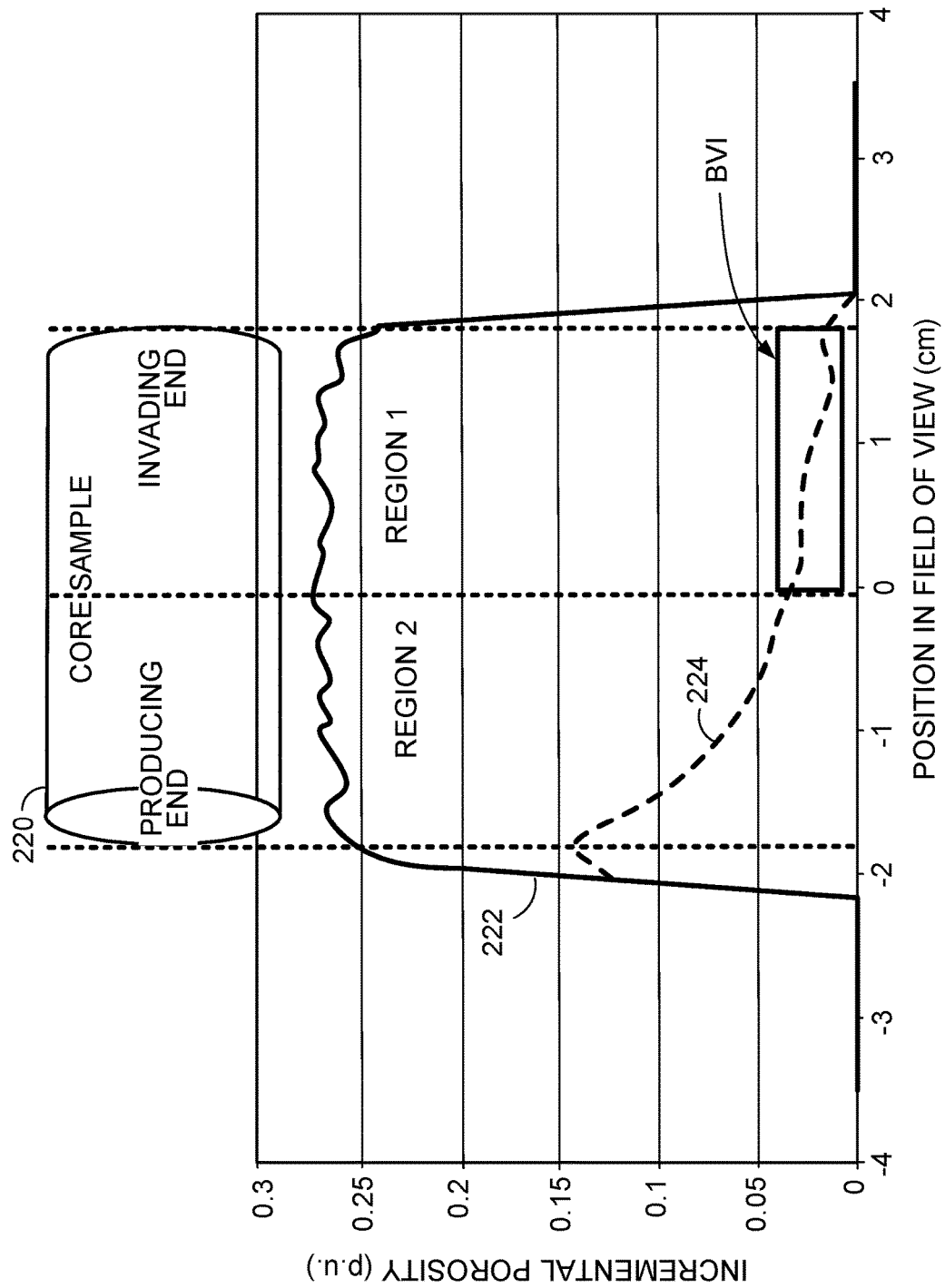
FIG. 3 shows saturation profiles of a sample under saturated conditions and after a low-saturation portion meets minimum length of the method of FIG. 1.

FIG. 3 show a core sample 220 and an associated plot of a saturation profile 222 measured under saturated conditions and a saturation profile 224 measured after the length of the low-saturation portion 226 of the sample exceeds the minimum criteria of the method described with respect to FIG. 1. The saturation profiles are shown as the porosity observed at different positions along the sample in the field of view of the NMR instrumentation. NMR techniques measure water content. Accordingly, the porosity before spinning the sample is at 100% saturation. Saturation along the sample after spinning the sample can be calculated by dividing the observed water content (reported as porosity) divided by the porosity at 100% saturation. In this field, the NMR results are typically reported as porosity and porosity is used a proxy for saturation.

FIGS. 4A, 4B, and 4C show components of a system operable to implement the method of FIG. 1. FIG. 4A shows a centrifuge, FIG. 4B shows an NMR system, and FIG. 4C shows a core sample.

Figure 5:
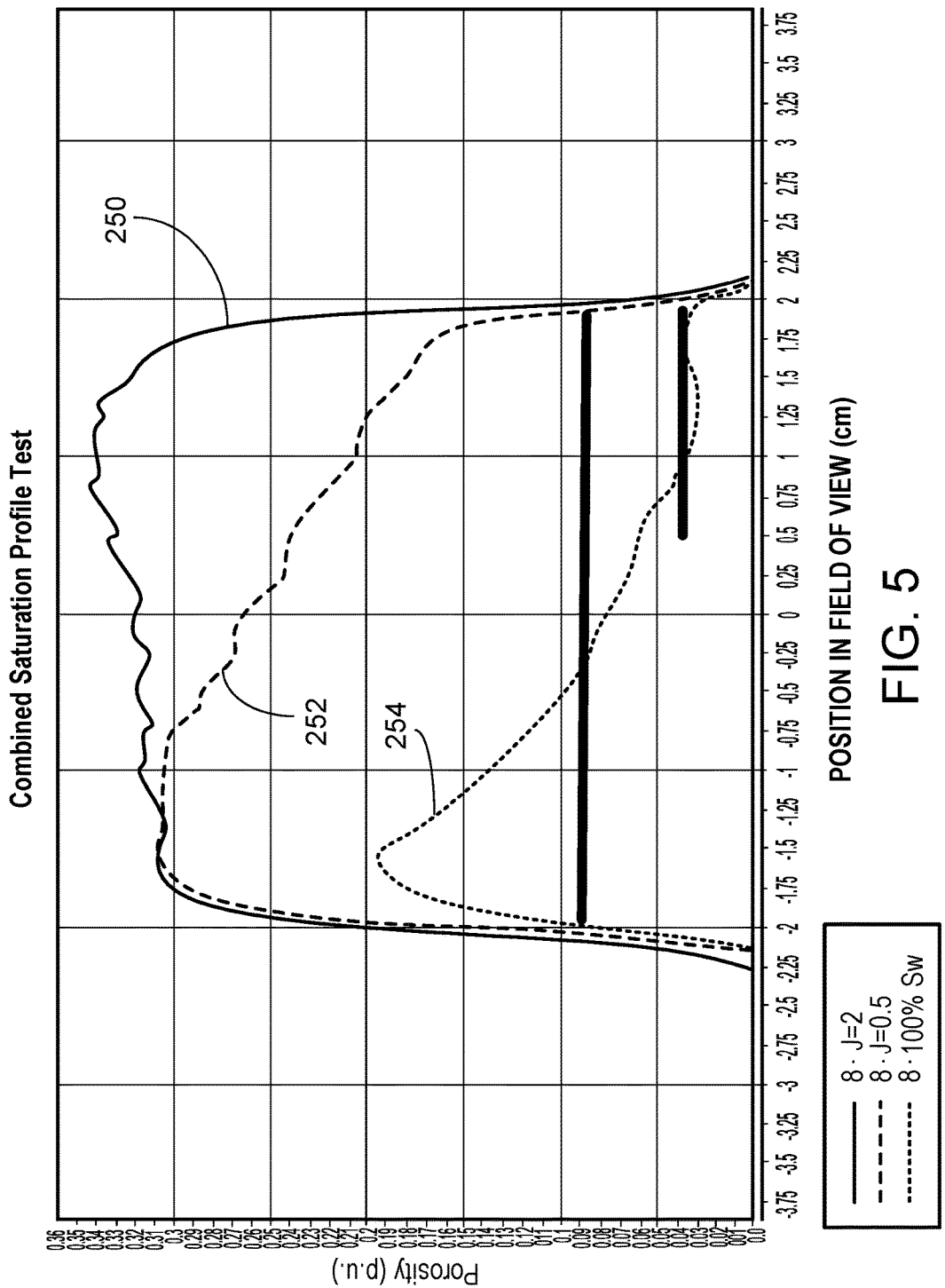
FIG. 5 shows saturation profiles of a low permeable carbonate core sample at 100% saturation, after spinning at 2800 RPM, and after spinning at 5600 RPM.

FIG. 5 shows a saturation profile 250 of a low permeability carbonate core sample measured at 100% saturation, a saturation profile 252 measured after spinning at 2800 revolutions per minute (RPM), and a saturation profile 254 measured after spinning at 5600 RPM. These results are consistent with the theory used in the capillary pressure by centrifuge in which the saturation is known to be non-uniform along the length of the sample during spinning. The average porosity of the sample is ~0.33 porosity units (p.u.). A 5% variation of the porosity/saturation is ~0.02 p.u. After spinning at 2800 RPM for ~6 hours, the porosity at a position of ~1.9 cm in the field of view was ~0.09 p.u. The porosity of 0.12 p.u. (~10% higher than the minimum porosity) was at ~1.8 cm in the field of view and the length of the low-saturation portion of the sample is ~0.1 cm.

As the length of the low-saturation portion of the sample was less than 1 cm, the sample was spun again at a higher rate. After the sample was spun at 5600 RPM for ~6 hours, the porosity at a position of ~1.9 cm in the field of view was ~0.03 p.u. The porosity of 0.06 p.u. (~10% higher than the minimum porosity) was at ~0.5 cm in the field of view and the length of the low-saturation portion of the sample was ~1.4 cm. As the length of the low-saturation portion of the sample was more than 1 cm, the $T_2$ spectrum of the of the low-saturation portion of the sample was measured and then used as the basis for estimation of the $T_2$ cutoff using the procedure explained later in this disclosure.

FIG. 5 also illustrates how using just properties measured in the low-saturation portion of the sample can provide a significantly improved result to using properties measured across the whole sample. The sample was considered at irreducible water state after 5600 RPM spinning since the low saturation at one end approached a stable value and further spinning at a higher RPM did not reduce the higher saturation much further due to capillary end effect. As can be seen from the saturation profile 252 and the saturation profile 254, the saturation distributions are far from uniform. The low-saturation portion of the sample has an average porosity of ~0.04 p.u. which approximates the real irreducible water saturation. In contrast, the average saturation across the whole sample is ~0.09 p.u. The average saturation is significantly higher the real irreducible water saturation and procedures that rely on the average saturation will significantly underestimate the recoverable reserve from a formation of the porous media.

Figure 6A:
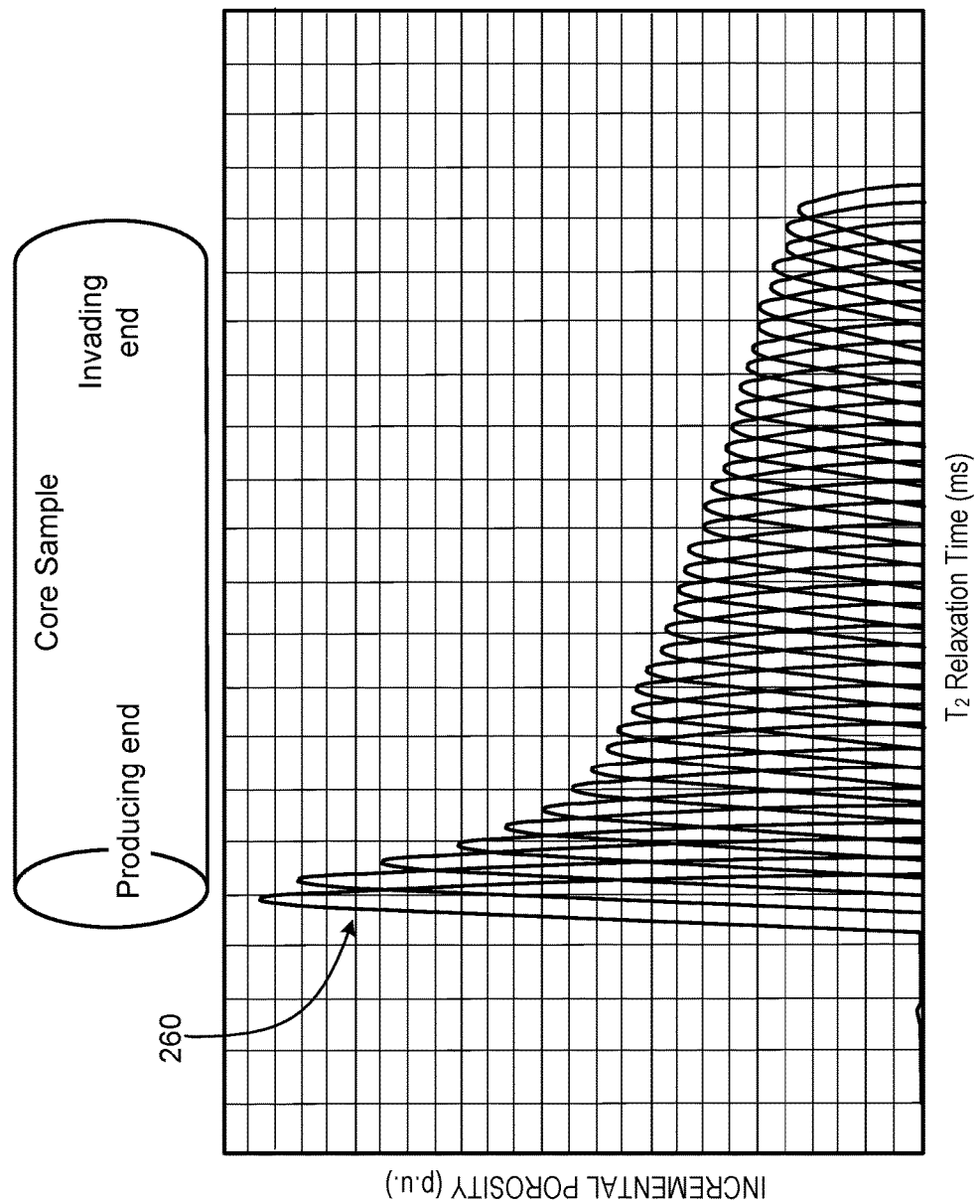
FIGS. 6A and 6B show $T_2$ spectra along a core sample after spinning.
Figure 6B:
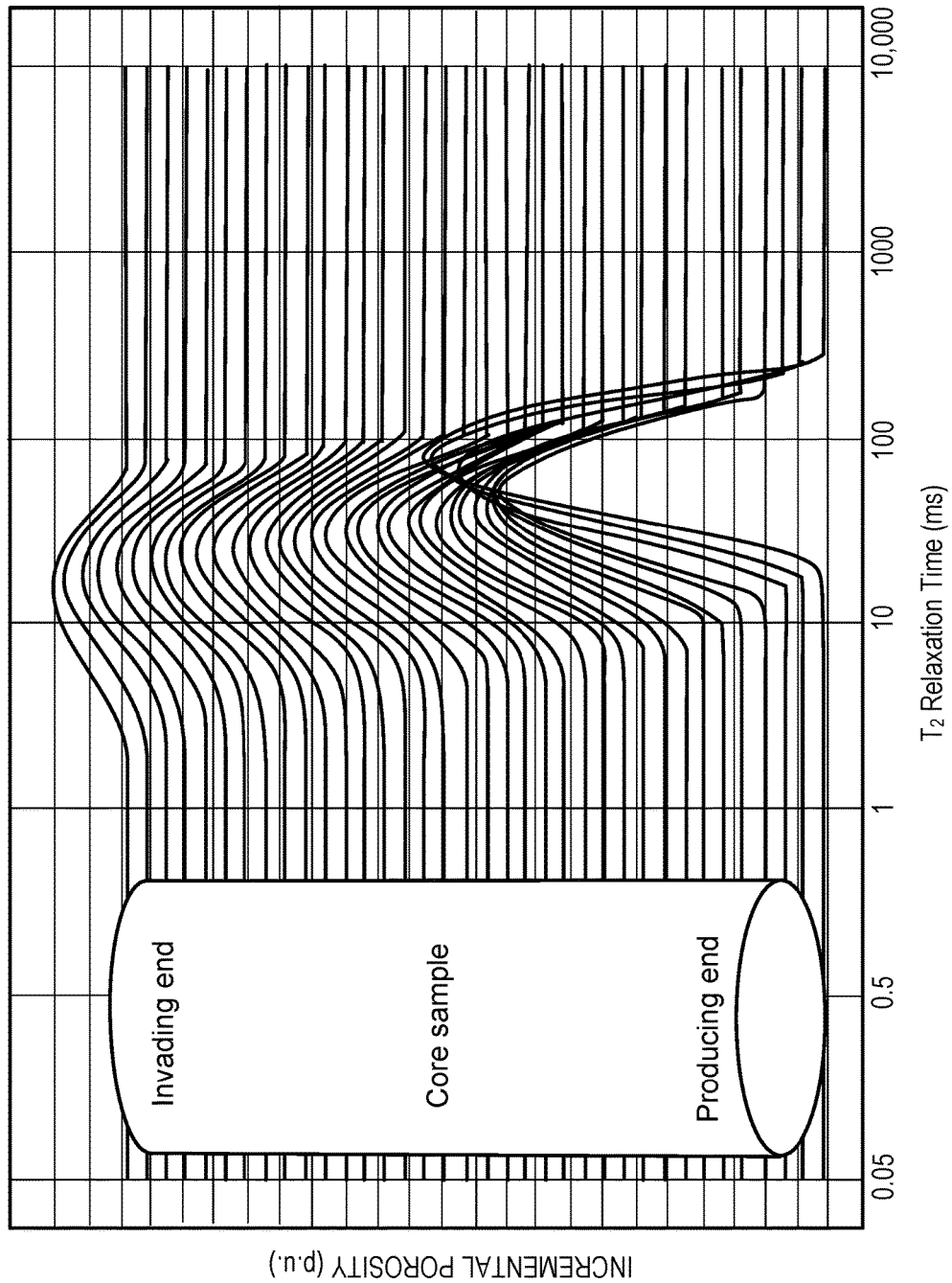

FIGS. 6A and 6B show the effect of the non-uniform distribution of saturation on a $T_2$ spectrum 260. The graphs in FIGS. 6A and 6B are spatial $T_2$ from another sample at an irreducible state produced by spinning in a centrifuge. The spatial $T_2$ provides $T_2$ distributions at many positions along the length of the sample. Similar to the graph in FIG. 5, the total amplitude (saturation) has a non-uniform distribution along the core (FIG. 6A) and the $T_2$ spectra of lower saturations (real irreducible saturation) shift to the left of the lower $T_2$ region (FIG. 6B). Methods which only perform one $T_2$ measurement on the whole core obtain the combination of all the spectra in FIGS. 6A and 6B including spectra from outside the low-saturation region. As a result, the $T_2$ spectrum of the whole core has larger amplitude and longer $T_{2mean}$. In summary, methods which only perform one $T_2$ measurement actually obtain the $T_2$ spectrum shifting to right (longer $T_2$) at a saturation significantly higher than real irreducible water saturation.

Accounting for the variation of saturation across the sample allows the method described with respect to FIG. 1 to produce more accurate results than methods which rely on the assumption that the saturation distribution along the core after desaturation is more or less uniform and the $T_2$ measurement is conducted on this uniform saturation. This assumption may be valid for porous plate desaturation methods since there should not be any pressure difference across the core when the equilibrium is reached. However, the method described with respect to FIG. 1 is much faster than porous plate desaturation methods and is not subject to the upper pressure limit restrictions on low permeable core samples that limit porous plate desaturation methods. These methods avoid the shortcomings of measuring $T_2$ at average saturation which is systematically higher than the real irreducible water saturation for low permeability samples.

Figure 7:
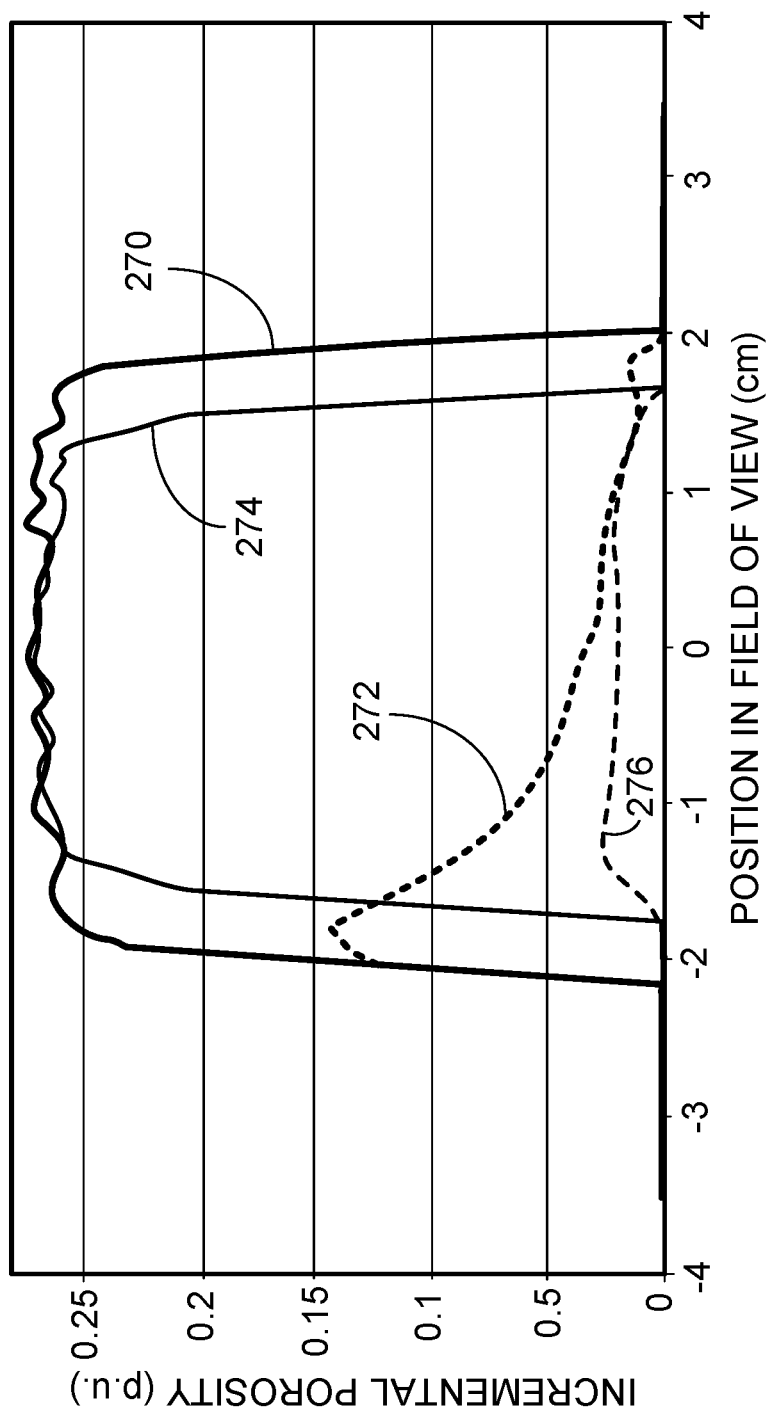
FIG. 7 compares saturation profiles for a high permeability sample and a low permeability sample.

FIG. 7 illustrates why this error is not as significant for high permeability samples. FIG. 7 compares a saturation profile 270 of a low permeability limestone core measured at 100% saturation, a saturation profile 272 of the low permeability limestone core measured at irreducible water saturation, and a saturation profile 274 of a high permeability limestone core measured 100% saturation, and a saturation profile 276 of the high permeability limestone core measured at irreducible water saturation. As discussed with respect to FIG. 5, the average porosity of the saturation profile 272 of the whole low permeability sample is much higher than the average porosity of the low-saturation portion of the profile. In contrast, the average porosity of the saturation profile 276 of the whole high permeability limestone core is very close to the saturation at the invading end of the sample.

The method described with respect to FIG. 1 also reduces the operational uncertainty associated with the selection of spinning speed to reach irreducible water saturation that can be partially attributed to the ambiguity of the concept of the BVI or non-movable water.

Figure 8A:
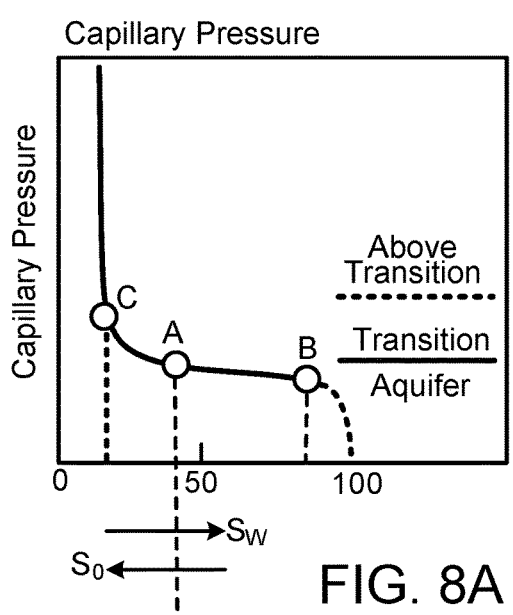
FIG. 8A illustrates the estimation of irreducible water saturation using a chart plotting capillary pressure as a function of saturation.
Figure 8B:
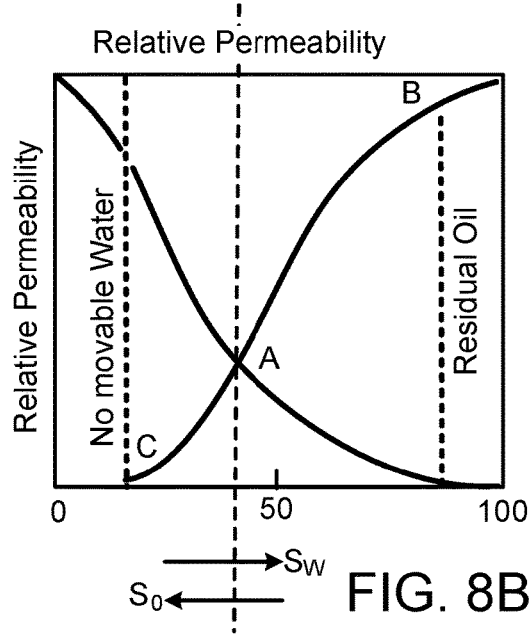
FIG. 8B illustrates the estimation of irreducible water saturation using a chart plotting relative permeability as a function of saturation.
Figure 8C:
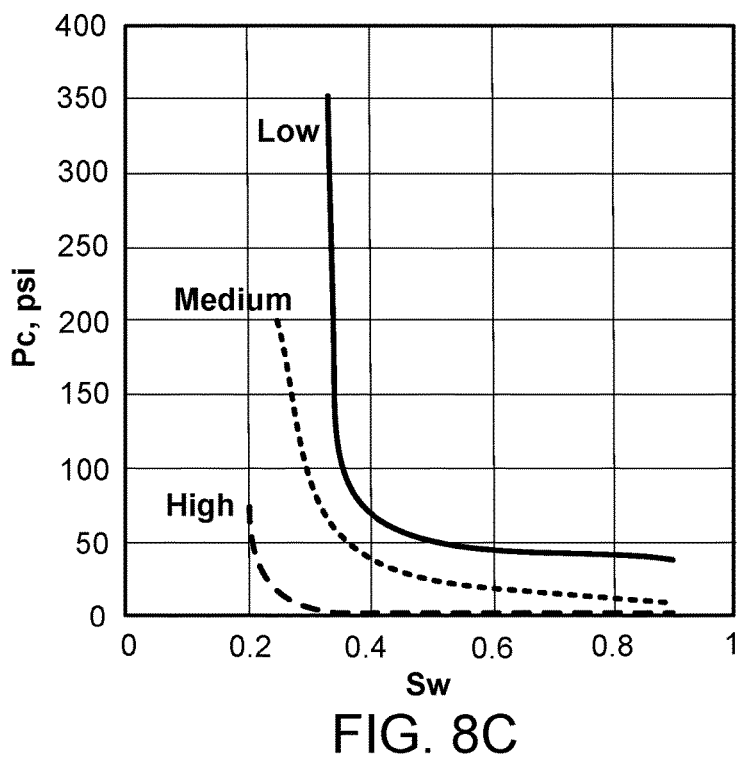
FIG. 8C illustrates typical capillary pressure curves for low, medium, and high permeability core samples.

FIG. 8A (https://www.spec2000.net/15-swirr.htm) presents capillary pressure as a function of saturation (Sw, So). FIG. 8B (https://www.spec2000.net/15-swirr.htm) presents relative permeability as a function of saturation. FIG. 8C illustrates typical capillary pressure curves for low, medium, and high permeability core samples. In well logging, the irreducible water is mostly related to the connate water saturation above the transition zone shown in FIG. 8A. In oil or gas zone, the connate or irreducible water is considered non-movable. The irreducible water saturation concept is also applied in obtaining capillary pressure and relative permeability even though the irreducible state is obtained by different processes (core flood for relative permeability and centrifuge or porous plate for capillary pressure). These values are usually equal or very close as shown in FIG. 8A and FIG. 8B, particularly for highly permeable samples. For the highly permeable sample whose capillary pressure curve is shown in FIG. 8C, a small capillary pressure (~50 psi) can remove almost all the movable water and there is no or very little water produced at a higher spinning speed indicated by the vertical part of the capillary curve. If the sample has a complex pore system or low permeability, the capillary pressure required to reach irreducible water saturation are higher and varies as shown with the medium and low permeability samples shown FIG. 8C.

There are several ways to obtain the suitable centrifuge spinning speed to reach irreducible state. If the petrophysicist who sends samples for testing has the displacement pressure of the formation, an appropriate spinning speed can be chosen to provide that known displacement pressure. Alternatively, most service laboratory select a spinning speed based on sample categories or simple correlation. For example, for sandstone, displacement pressure of 100 psi is used for high permeable samples, 200 psi for medium to low permeable samples and 300 psi for ultra-low permeable samples and 400 psi for carbonate samples. The rock density or J function is also used to select the spinning speed. The selected speed using these simple correlations can easily above or below the right speed. If permitted, an additional higher speed can be used and the incremental production can be measured to verify the irreducible state. If the production continues, further verification can be performed at even higher speeds. It is basically a trial and error method which increase time required and testing costs.

In contrast, identifying and measuring properties of the low-saturation portion of a sample enables selection of the displacement pressures or spinning speeds to reach the irreducible saturation by quantitative criteria instead of by trial and error. This approach is especially useful for the core samples with complex pore systems as shown in FIG. 8C. For these core samples, the incremental production may not approach zero with increasing spinning speeds, which makes the identification of irreducible water state difficult. In addition, the quantitative selection of spinning speed described in this disclosure avoids the extra steps involved in determining the irreducible state by increasing the spinning speed and check the mass loss for verification. In the trial and error approach, the incremental production is mainly from the high saturation end while there is little change to the low-saturation end.

The improved accuracy provided by methods which identify and measure properties of the low-saturation portion of a sample are anticipated to occur mainly on the measurements on medium to low permeability core samples and core samples with complex pore systems.

For homogenous samples, determining porous media properties based on characteristics of a portion of each sample is generally appropriate. However, for heterogeneous samples, different portions of a sample have different properties and determining porous media properties based on characteristics of a portion of each sample can be problematic.

Figure 9:
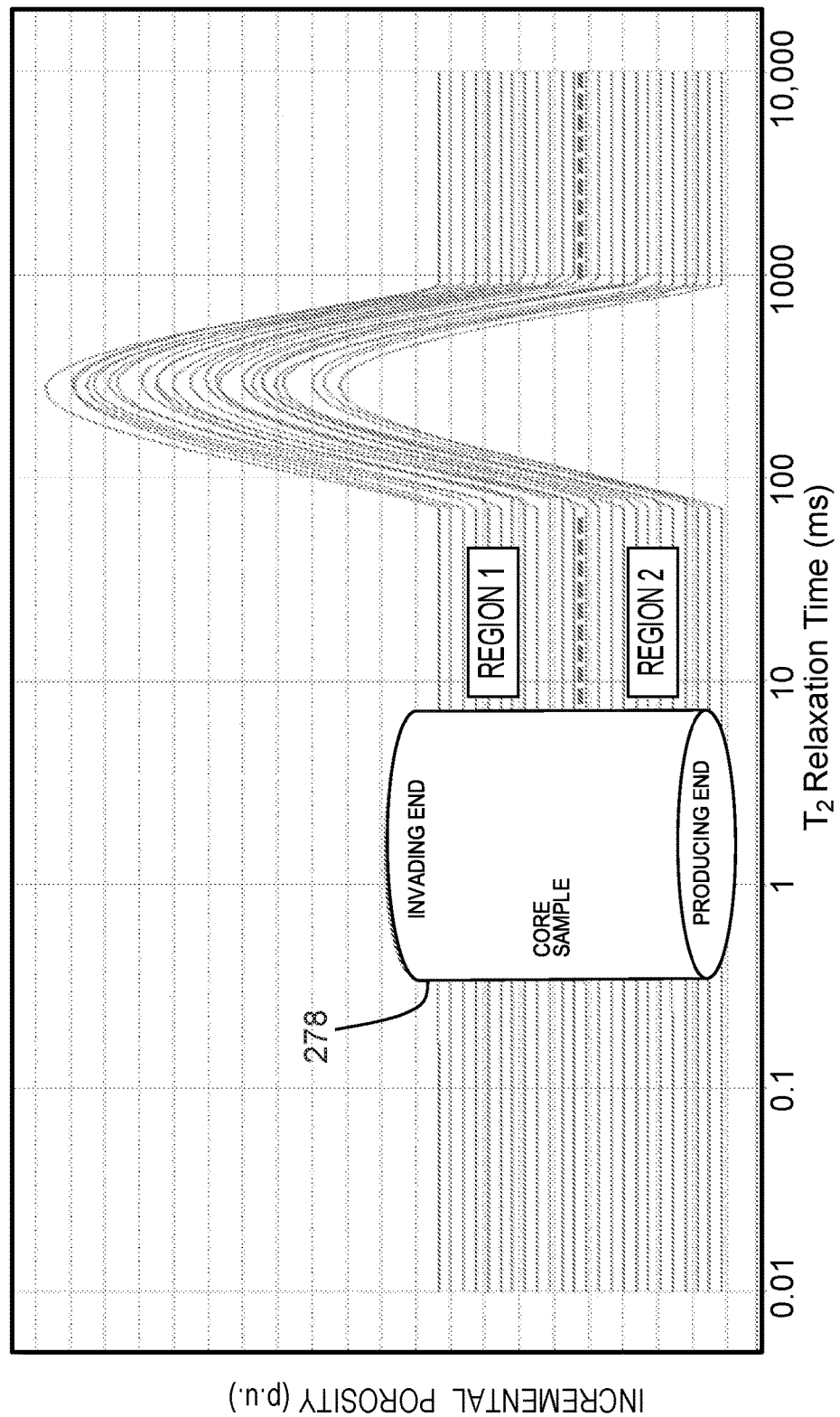
FIG. 9 shows a spatial-$T_2$ of the homogeneous limestone core sample at 100% water saturation.
Figure 10:
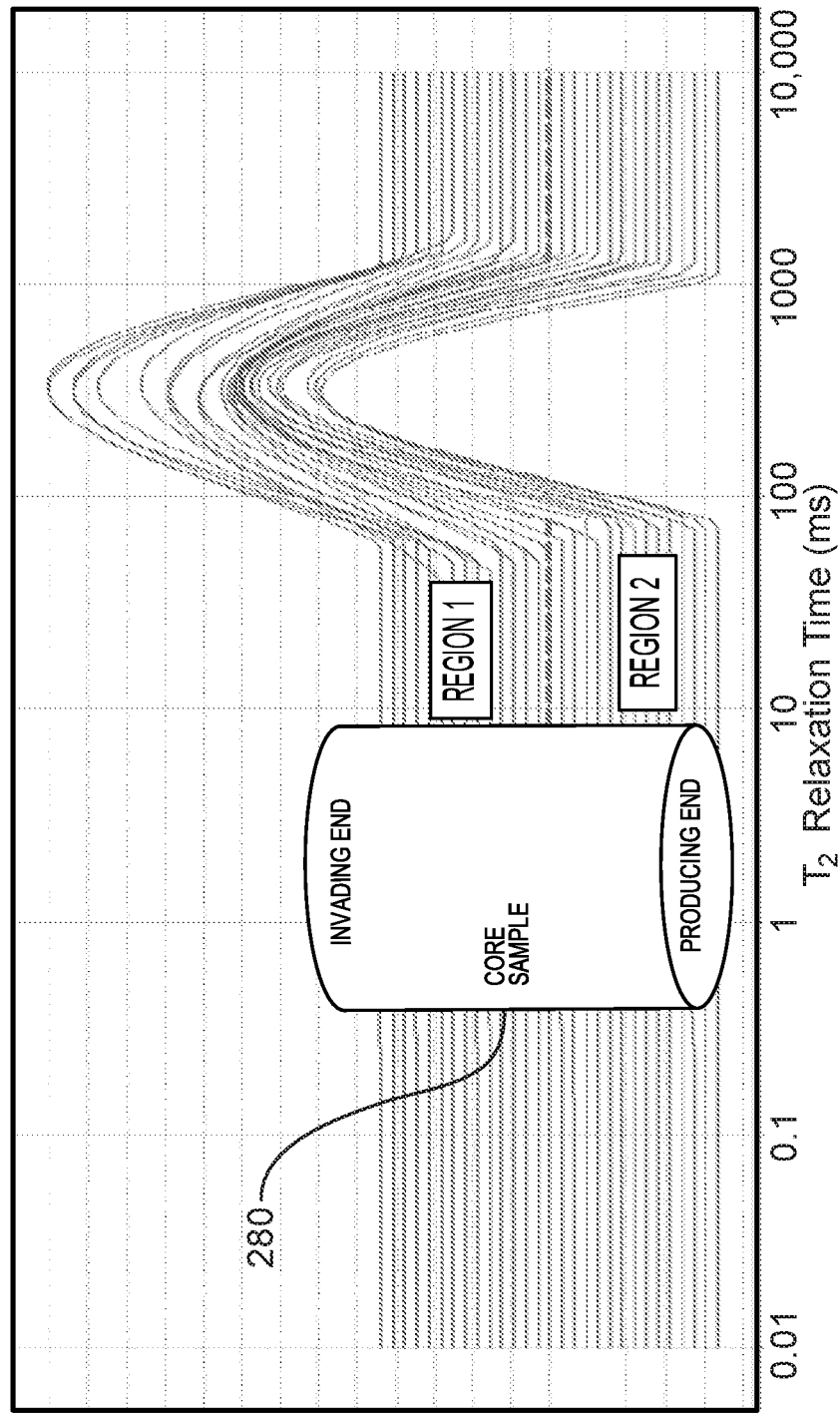
FIG. 10 shows a spatial-$T_2$ of less homogeneous limestone core sample at 100% water saturation.

For example, FIG. 9 shows a spatial-$T_2$ of the homogeneous limestone sample 278 and FIG. 10 shows a spatial-$T_2$ of the heterogeneous limestone sample 280. For the homogeneous limestone sample 300, applying the method described with respect to FIG. 1 would have approximately same result with the sample oriented as shown or with the sample reversed. In contrast, applying the method described with respect to FIG. 1 to heterogeneous limestone sample 280 would have different results with the sample oriented as shown and with the sample reversed.

Figure 11:
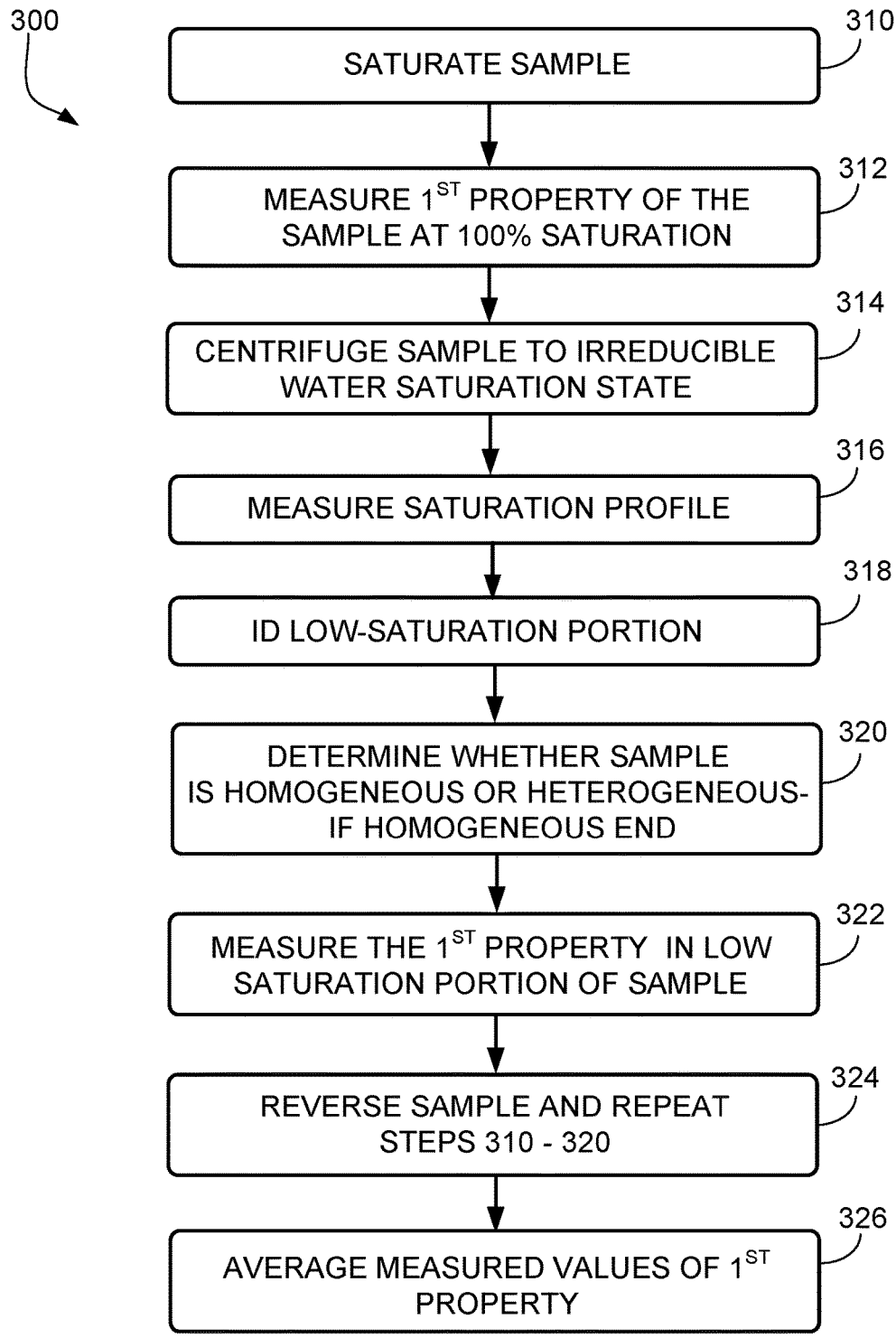
FIG. 11 illustrates a method of determining properties of a sample.

FIG. 11 illustrates a method 300 of determining a property of a porous media based on measurements in a low-saturation portion of the sample. The method 308 includes saturating a sample of the porous media with a fluid 310. A first property of the porous media is measured on the saturated sample 312 if characteristics at saturation are used in subsequent calculations. The sample is spun in a centrifuge to remove fluid 314. After spinning, a saturation profile of the sample is measured 316 and used to identify a low-saturation portion of the sample 318. The first property of the porous media is measured in the identified portion of the sample 320. Optionally, determine whether the sample is homogenous or heterogeneous 322. This determination can be performed by visual analysis of the spatial $T_2$. The fluctuation of the saturation profile at 100% water saturation indicates the degree of the homogeneity. For example, if the maximum porosity is more than 10% greater (e.g., more than 20% greater, more than 30% greater, or more than 40% greater) than the minimum porosity, the sample is considered to be heterogeneous.

If the sample is homogenous, use the measured first property as the determined value of the first property. If the sample is heterogeneous or the homogeneous/heterogeneous determination is not performed, reverse the sample in the centrifuge, repeat steps 310-320, and use an average of the measured values of the first property as the determined first property.

In one application, the method 300 can be applied to a core sample from a formation to estimate the $T_2$ cutoff of the formation. A cleaned and dried core sample from a formation of interest is saturated with brine. After saturation, NMR techniques are used to obtain a saturation profile and a $T_2$ spectrum of the saturated sample. The sample is spun in a centrifuge to achieve an irreducible water saturation state. After spinning, a saturation profile of the sample is measured using NMR techniques and used to identify a low-saturation portion of the sample.

BVI is estimated from the low-saturation portion of the sample close to invading end that shows saturation variations between its two ends for maximum of 10%. The length of this region is recommended to cover almost half of the sample length. This can be achieved by gradually increasing centrifuge speed and repeating the spinning and measuring steps. Alternatively, the quantitative approach described above with respect to FIG. 1 can be used to provide an appropriate spinning speed and identify the low-saturation portion of the sample.

The $T_2$ distributions within the low-saturation region of BVI are summed to get single $T_2$ distribution and a cumulative porosity for the single $T_2$ distribution is plotted. The $T_2$ spectrum and associated cumulative curve of the low-saturation portion spectrum are compared with the $T_2$ spectrum and associated cumulative curve as observed for the same portion of the core at 100% saturation to determine the $T_2$ cutoff. This approach is anticipated to be more appropriate for heterogeneous samples than the approach of converting the $T_2$ spectrum of the low-saturation portion to the whole core by a ratio of core length to the low-saturation portion length as previously described with respect to the method 100.

For homogeneous samples, this $T_2$ cutoff is determined to be the $T_2$ cutoff for the porous media being analyzed. For heterogeneous samples, the sample is reversed in the centrifuge and the process is repeated to produce a second estimate of the $T_2$ cutoff. The average of the two estimated values of the $T_2$ cutoff is determined to be the $T_2$ cutoff for the porous media being analyzed.

Figure 12A:
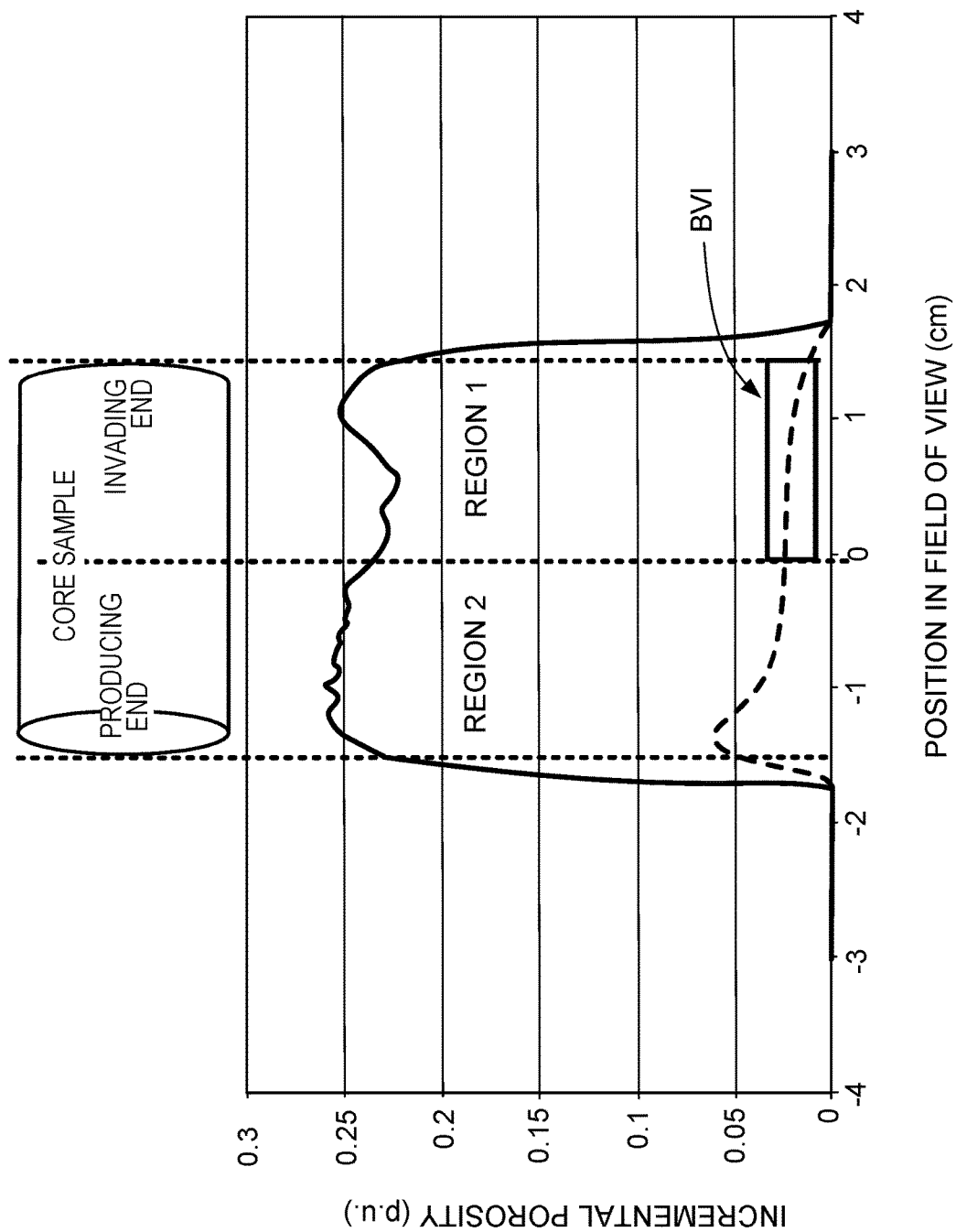
FIGS. 12A and 12B show saturation profiles for a heterogeneous core sample in two orientations.
Figure 12B:
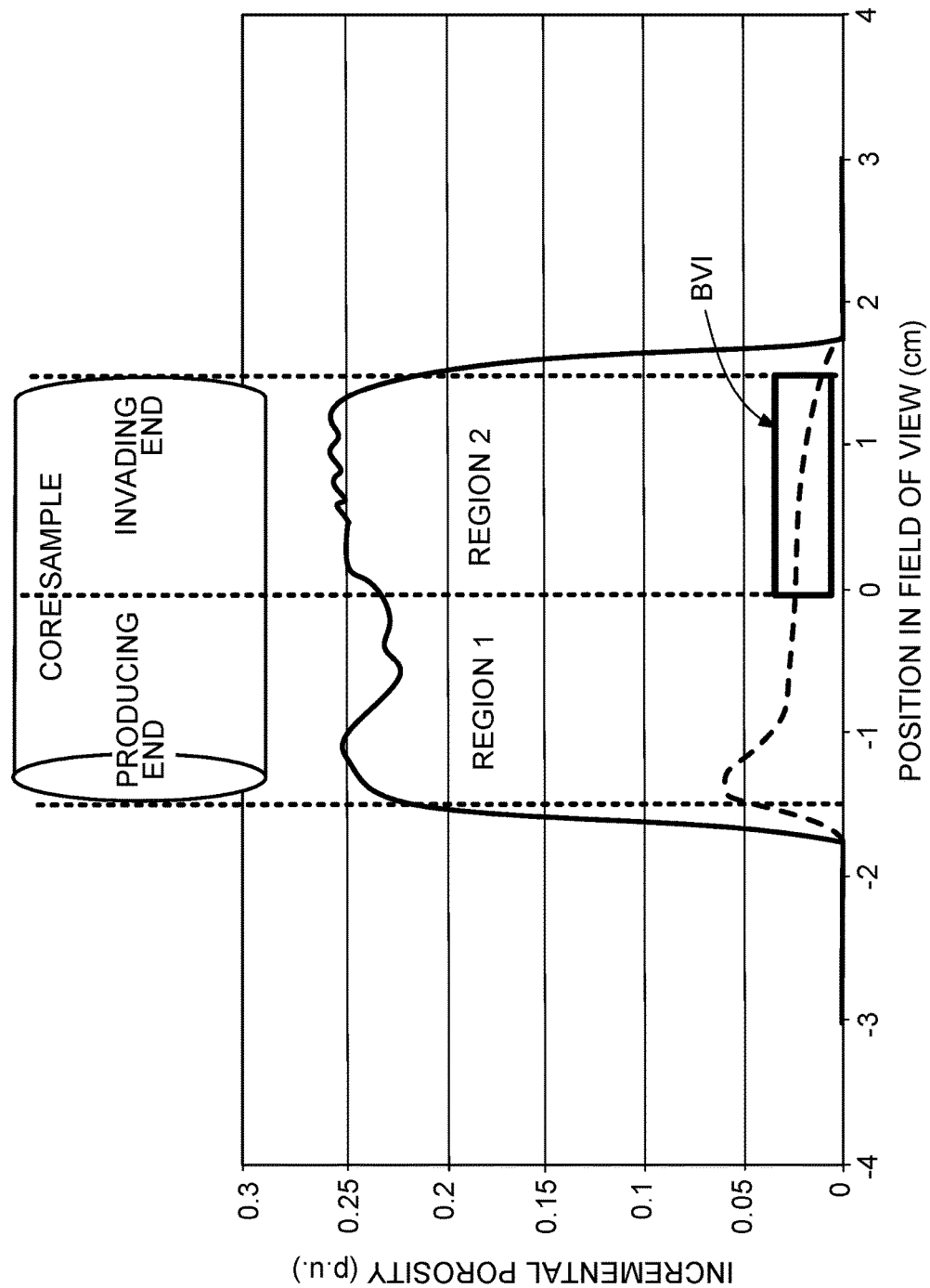

FIGS. 12A and 12B illustrate the impact of the method 300. FIG. 12A shows saturation curves for 100% saturation and irreducible water saturation conditions for a heterogeneous sample. FIG. 12B shows saturation curves for 100% saturation and irreducible water saturation conditions for the same heterogeneous sample after it has been reversed. Using only the initial analysis, the $T_2$ cutoff is estimated to be 115 ms. Based on an average of the initial and the reversed sample analysis, the $T_2$ cutoff is estimated to be 80 ms. This would result in a 7% difference in the estimated recoverable reserves for the formation of interest.

A number of embodiments of the invention have been described. Nevertheless, it will be understood that various modifications may be made without departing from the spirit and scope of the invention. Accordingly, other embodiments are within the scope of the following claims.

What is claimed is:

1. A method of estimating a $T_2$ cutoff of a porous media, the method comprising:
saturating a sample of the porous media with a fluid;
measuring a spatial $T_2$ distribution of the sample while saturated;
preparing the sample for unsaturated measurement by:
spinning the sample in a centrifuge with a first end of the sample closer to an axis of rotation of the centrifuge than a second end of the sample;
obtaining a saturation profile of the sample; and
identifying a first low-saturation portion of the sample;
measuring a spatial $T_2$ distribution of the porous media on the first low-saturation portion of the sample;
obtaining a first estimate of the $T_2$ cutoff of the porous media by comparing the spatial $T_2$ distribution measured on the first low-saturation portion of the sample with the spatial $T_2$ distribution measured under saturated conditions;
saturating the sample of the porous media with the fluid;
measuring a spatial $T_2$ distribution of the sample while saturated;
preparing the sample for unsaturated measurement by:
spinning the sample in a centrifuge with the second end of the sample closer to the axis of rotation of the centrifuge than the first end of the sample;
obtaining a saturation profile of the sample; and
identifying a second low-saturation portion of the sample;
measuring a spatial $T_2$ distribution of the porous media on the second low-saturation portion of the sample;
obtaining a second estimate of the $T_2$ cutoff of the porous media by comparing the spatial $T_2$ distribution measured on the second low-saturation portion of the sample with the spatial $T_2$ distribution measured under saturated conditions; and
averaging the first estimate of the $T_2$ cutoff and the second estimate of the $T_2$ cutoff.

2. The method of claim 1, wherein obtaining the saturation profile of the sample comprises performing NMR measurements on the sample.

3. The method of claim 1, comprising determining that the sample is heterogeneous.

4. The method of claim 3, wherein determining that the sample is heterogeneous comprises comparing a maximum porosity and a minimum porosity of the sample.

5. The method of claim 1, wherein identifying the first low-saturation portion of the sample comprises identifying a portion of the sample in which saturation of the sample is within 10% of a minimum saturation of that portion of the sample.

6. The method of claim 1, wherein comparing the spatial $T_2$ distribution measured on the first low-saturation portion of the sample with the spatial $T_2$ distribution measured under saturated conditions comprises comparing the spatial $T_2$ distribution measured on the first low-saturation portion of the sample with a portion of the spatial $T_2$ distribution measured under saturated conditions that corresponds with the first low-saturation portion of the sample.

7. A method of estimating a $T_2$ cutoff of a porous media, the method comprising:
saturating a sample of the porous media with a fluid;
measuring a spatial $T_2$ distribution of the sample while saturated;
preparing the sample for unsaturated measurement by:
spinning the sample in a centrifuge with a first end of the sample closer to an axis of rotation of the centrifuge than a second end of the sample;
obtaining a saturation profile of the sample; and
identifying a first low-saturation portion of the sample;
measuring a spatial $T_2$ distribution of the porous media on the first low-saturation portion of the sample; and
obtaining a first estimate of the $T_2$ cutoff of the porous media by comparing the spatial $T_2$ distribution measured on the first low-saturation portion of the sample with the spatial $T_2$ distribution measured under saturated conditions.

8. The method of claim 7, comprising determining that the sample is heterogeneous.

9. The method of claim 8, comprising:
saturating the sample of the porous media with the fluid;
measuring a spatial $T_2$ distribution of the sample while saturated;
preparing the sample for unsaturated measurement by:
spinning the sample in a centrifuge with the second end of the sample closer to the axis of rotation of the centrifuge than the first end of the sample;
obtaining a saturation profile of the sample;

identifying a second low-saturation portion of the sample;

measuring a spatial $T_2$ distribution of the porous media on the second low-saturation portion of the sample;

obtaining a second estimate of the $T_2$ cutoff of the porous media by comparing the spatial $T_2$ distribution measured on the second low-saturation portion of the sample with the spatial $T_2$ distribution measured under saturated conditions; and averaging the first estimate of the $T_2$ cutoff and the second estimate of the $T_2$ cutoff.

10. The method of claim 9, wherein obtaining the saturation profile of the sample comprises performing NMR measurements on the sample.

11. The method of claim 9, wherein identifying the first low-saturation portion of the sample comprises identifying a portion of the sample in which saturation of the sample is within 10% of a minimum saturation of that portion of the sample.

12. The method of claim 9, wherein comparing the spatial $T_2$ distribution measured on the first low-saturation portion of the sample with the spatial $T_2$ distribution measured under saturated conditions comprises comparing the spatial $T_2$ distribution measured on the first low-saturation portion of the sample with a portion of the spatial $T_2$ distribution measured under saturated conditions that corresponds with the first low-saturation portion of the sample.

13. A method of estimating a property of a porous media, the method comprising:

saturating a sample of the porous media with a fluid;

spinning the sample in a centrifuge with a first end of the sample closer to an axis of rotation of the centrifuge than a second end of the sample;

measuring a first property of the porous media to obtain a first estimate of the first property;

saturating the sample of the porous media with the fluid after obtaining the first estimate of the first property;

spinning the sample in a centrifuge with the second end of the sample closer to the axis of rotation of the centrifuge than the first end of the sample;

measuring the first property of the porous media to obtain a second estimate of the first property; and determining the second property of the porous media based at least in part on the first estimate of the first property and the second estimate of the first property.

14. The method of claim 13, comprising determining that the sample is heterogeneous.

15. The method of claim 13, comprising measuring the first property of the porous media after saturating the sample and before spinning the sample to obtain the first estimate of the first property.

16. The method of claim 13, wherein the first property and the second property are different properties.

17. The method of claim 16, wherein the first property is a spatial $T_2$ distribution.

18. The method of claim 17, wherein the second property is a $T_2$ cutoff of the porous media.

19. The method of claim 13, wherein determining the second property of the porous media comprises calculating a first estimate of the second property based on the first estimate of the first property, calculating a second estimate of the second property based on the second estimate of the first property, and averaging the first estimate of the second property and the second estimate of the second property.

20. The method of claim 13, wherein measuring a first property of the porous media to obtain a first estimate of the first property comprises identifying a low-saturation portion of the sample and measuring a first spatial $T_2$ distribution of the porous media on the identified portion of the sample.

21. The method of claim 20, wherein measuring a first property of the porous media to obtain a second estimate of the first property comprises identifying a low-saturation portion of the sample and measuring a second spatial $T_2$ distribution of the porous media on the identified portion of the sample.

22. The method of claim 21, comprising calculating a first estimate of a $T_2$ cutoff of the porous media based the first spatial $T_2$ distribution, calculating a second estimate of the $T_2$ cutoff of the porous media based the first spatial $T_2$ distribution of the porous media, and averaging the first estimate of the $T_2$ cutoff and the second estimate of the $T_2$ cutoff.

23. The method of claim 20, wherein identifying the low-saturation portion of the sample comprises performing NMR measurements on the sample.

* * * * *